US012758562B2

(12) United States Patent
Palermo et al.

(10) Patent No.: US 12,758,562 B2
(45) **Date of Patent: *Oct. 13, 2026**

(54) SYNTHESIS AND PROCESSING OF POLY(PRO-DRUG) MATERIALS FOR EXTENDED DRUG RELEASE AND USES THEREOF

(71) Applicant: RENSSELAER POLYTECHNIC INSTITUTE, Troy, NY (US)

(72) Inventors: Edmund Francis Palermo, Delmar, NY (US); Anthony Richard D'Amato, Troy, NY (US); Ryan J. Gilbert, Cohoes, NY (US); Samuel Ellman, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 1181 days.

This patent is subject to a terminal disclaimer.

(21) Appl. No.: 17/515,861

(22) Filed: Nov. 1, 2021

(65) Prior Publication Data

US 2022/0117976 A1 Apr. 21, 2022

Related U.S. Application Data

(63) Continuation-in-part of application No. 17/285,544, filed as application No. PCT/US2019/056539 on Oct. 16, 2019, now Pat. No. 11,202,834.

(60) Provisional application No. 63/174,091, filed on Apr. 13, 2021, provisional application No. 62/912,744, filed on Oct. 9, 2019, provisional application No. 62/746,243, filed on Oct. 16, 2018.

(51) Int. Cl.

| | |
|---|---|
| ***A61K 31/566*** | (2006.01) |
| ***A61K 31/12*** | (2006.01) |
| ***A61K 31/135*** | (2006.01) |
| ***A61K 47/56*** | (2017.01) |

(52) U.S. Cl.
CPC ............ *A61K 31/566* (2013.01); *A61K 31/12* (2013.01); *A61K 31/135* (2013.01); *A61K 47/56* (2017.08)

(58) Field of Classification Search
CPC .................................................... A61K 31/566
See application file for complete search history.

(56) References Cited

U.S. PATENT DOCUMENTS

| | | | | |
|---|---|---|---|---|
| 5,653,992 | A | 8/1997 | Bezwada et al. | |
| 6,306,166 | B1 | 10/2001 | Barry et al. | |
| 8,394,409 | B2 | 3/2013 | Odidi et al. | |
| 8,948,863 | B2 | 2/2015 | Kraft et al. | |
| 8,969,415 | B2 | 3/2015 | Robinson et al. | |
| 9,730,885 | B2 | 8/2017 | Gower et al. | |
| 10,143,659 | B2 | 12/2018 | Park et al. | |
| 11,202,834 | B2 * | 12/2021 | Palermo | A61K 9/70 |
| 2008/0220054 | A1 | 9/2008 | Shastri et al. | |
| 2010/0190933 | A1 | 7/2010 | Zhao et al. | |
| 2015/0010630 | A1 | 1/2015 | Llamas et al. | |
| 2017/0168041 | A1 | 6/2017 | Liu et al. | |

FOREIGN PATENT DOCUMENTS

WO 2013013038 A2 1/2013

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Wolff, Burger's medicinal Chemistry and Drug Discovery, vol. 1, Principles and Practice, John Wiley & sons, New York, 1997.*
Zhang, "Facile Fabrication of 10-Hydroxycamptothecin-Backboned Amphiphilic Polyprodrug with Precisely Tailored Drug Loading Content for Controlled Release," Bioconjugate Chemistry, vol. 29, pp. 2239-2247, May 30, 2018.*
Xu, "Smart and hyper-fast responsive polyprodrug nanoplatform for targeted cancer therapy,".*
International Search Report and the Written Opinion of the International Searching Authority, International Application No. PCT/US2019/056539, mailed Feb. 12, 2020.

(Continued)

*Primary Examiner* — Nizal S Chandrakumar
(74) *Attorney, Agent, or Firm* — Barclay Damon LLP; Anthony P. Gangemi

(57) ABSTRACT

The poly(pro-drug) material includes one or more alternating therapeutic compounds and biodegradable hydrocarbyl groups. The therapeutic compounds and biodegradable hydrocarbyl groups are separated by cleavable linker compounds. The therapeutic compounds, such as estrogen, curcumin, and fingolimod, include a plurality of substitutable functional groups that provide reaction sites for complexing with the cleavable linkers and in turn one or more polymers, such that the poly(pro-drug) material ends up composed of the therapeutic compound itself. In aqueous media and at physiological temperature and pH, the poly(pro-drug) materials degrade to release the therapeutic compounds from the material with a zero-order release profile, Advantageously, the poly(pro-drug) materials release the therapeutic compounds on time scales of years. The poly(pro-drug) materials also exhibit reduced to allow for prolonged implantation within a patient. These materials are enticing for a myriad of biomedical applications, including veterinary medicine, cancer treatments, birth control, and hormone replacement therapy.

2 Claims, 11 Drawing Sheets

(56) References Cited

OTHER PUBLICATIONS

Zhang, X., et al., "Facile Fabrication of 10-Hydroxycamptothecin-Backboned Amphiphilic Polyprodrug with Precisely Tailored Drug Loading Content for Controlled Release," Bioconjugate Chemistry, vol. 29, pp. 2239-2247, May 30, 2018.
Patel, B.B., et al., "Curcumin Targets FOLFOX-surviving Colon Cancer Cells via Inhibition of EGFRs and IGF-1R," Anticancer Research, vol. 30, pp. 319-326, Feb. 2010.
Xu, X.D., et al., "Smart and hyper-fast responsive polyprodrug nanoplatform for targeted cancer therapy," Biomaterials, vol. 76, pp. 238-249, Oct. 23, 2015.
D'Amato, A.R., et al., "Vastly extended drug release from poly(pro-17β-estradiol) materials facilitates in vitro neurotrophism and neuroprotection," Nature Communications, vol. 10, pp. 1-12, Oct. 23, 2019.

* cited by examiner

SYNTHESIS AND PROCESSING OF POLY(PRO-DRUG) MATERIALS FOR EXTENDED DRUG RELEASE AND USES THEREOF

CROSS REFERENCE TO RELATED APPLICATIONS

This application is a continuation-in-part application of U.S. Utility patent application Ser. No. 17/285,544, filed Apr. 15, 2021, which is a national stage filing of International Application No. PCT/US2019/056539, filed Oct. 16, 2019, which claims the benefit of U.S. Provisional Patent Application Nos. 62/912,744, filed on Oct. 9, 2019, and 62/746,243, filed on Oct. 16, 2018, which are incorporated by reference as if disclosed herein in their entirety. This application also claims the benefit of U.S. Provisional Patent Application No. 63/174,091, filed Apr. 13, 2021, which is incorporated by reference as if disclosed herein in its entirety.

STATEMENT REGARDING FEDERALLY SPONSORED RESEARCH AND DEVELOPMENT

This invention was made with U.S. Government support under Grant Number NS092754 awarded by the National Institutes of Health. The United States Government has certain rights in the invention.

BACKGROUND

Injuries to the Central Nervous System (CNS), including Spinal Cord Injury (SCI) and Traumatic Brian Injury (TBI), present some of the most notoriously retractable problems in modern medicine. For example, SCI affects approximately 17,000 patients per year in the USA, with dismally poor clinical outcomes; some extent of tetraplegia or paraplegia occurs in 99.2% of patients. Compelling epidemiological evidence suggests that females have significant SCI recovery advantages, relative to males. Interestingly, the major female sex hormone, 17β-Estradiol (E2), exhibits neurotrophic and neuroprotective effects, which might contribute to functional recovery. E2 reduces inflammation, glial cell reactivity, oxidative stress, and glutamate excitotoxic neuronal death, while also providing neurotrophism in the CNS. Since traumatic CNS injuries persist for years after the initial insult, there is an urgent unmet need for contact guidance scaffolds capable of releasing neuroprotective and regenerative drugs for this long duration.

Estrogen therapies are commonly used by doctors and veterinarians for these and other medical applications. Currently, the majority of products that provide extended release of estrogen are hormonal birth control products that deliver estrogen over time via diffusion Estring® (Pfizer Health AB, Sweden) and Nuvaring® (Merck Sharp & Dohme B. V. Besloten Vennootschap, Netherlands). Estring®, for example, releases estrogen for approximately 90 days before needing to be removed from a patient and replaced. Other biomaterial estrogen delivery approaches consist of incorporating estrogen into polymeric nanospheres for diffusive estrogen release. This approach, however, has only provided estrogen release for as long as 8 days, and requires co-loading with the protein albumin to achieve this release duration. Estrogen is also commonly delivered orally using drugs like Premarin® (Wyeth LLC, Delaware) or Menest® (Monarch Pharmaceuticals, LLC, Tennessee).

Pharmaceutical estrogen delivery approaches also include pro-drug formulations of estrogen. Pro-drugs of estrogen are widespread and currently in clinical use for hormonal therapy, breast and prostate cancers, breast enhancement, treatment of menopause symptoms, and birth control. The vast majority are alkyl esters (e.g., estradiol cypionate, estradiol valerate, estradiol benzoate, estradiol undecylate) administered by intramuscular injection. Typically they are injected once per month with a half-life of ~5 days. Polyestradiol phosphate (PEP), brand name Estradurin® (Ayerst Laboratories, Delaware), is an oligomeric pro-drug of estrogen composed of phosphate bonds. This pro-drug is administered in oil by intramuscular injection, once per month. The polymers are relatively ill-defined short oligomers with extensive chain branching. The average number of estrogen molecules in one Estradurin® oligomer is approximately 13. Estradurin® is currently discontinued in the United States.

SUMMARY

Some embodiments of the present disclosure are directed to a poly(pro-drug) material comprising one or more polymers according to Formula I:

(Formula I)

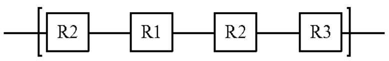

In some embodiments, R1 includes one or more therapeutic compounds. In some embodiments, R2 includes one or more cleavable linker compounds. In some embodiments, R3 includes one or more biodegradable hydrocarbyl groups. In some embodiments, the therapeutic compound includes an estrogen, curcumin, fingolimod, or combinations thereof. In some embodiments, the cleavable linker compound includes an ester, a urethane, a carbonate, or combinations thereof bound to the therapeutic compound. In some embodiments, the biodegradable hydrocarbyl group includes a hydrocarbyl chain having at least two carbons. In some embodiments, the biodegradable hydrocarbyl group includes polyethylene glycol), polyethylene glycol)) dithiol, or combinations thereof. In some embodiments, the material has a therapeutic compound release rate of about 0.01% and about 0.25% per day at physiological temperature and pH. In some embodiments, the one or more polymers have a molecular weight between about 80 kDa and about 90 kDa. In some embodiments, the one or more polymers include the structure according to Formula II:

(Formula II)

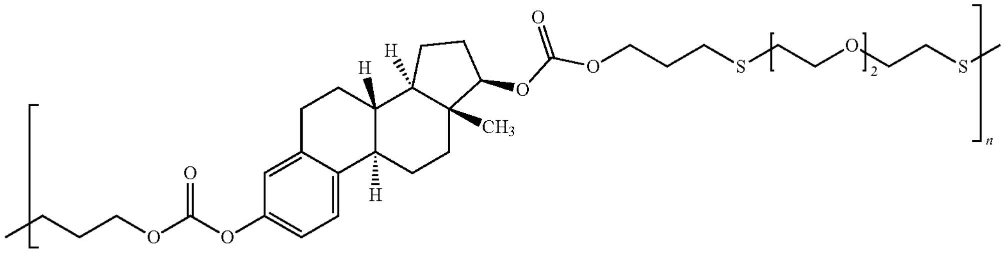

In some embodiments, n is greater than about 25.

Some embodiments of the present disclosure are directed to a method of making a poly(pro-drug) material. In some embodiments, the method includes providing a reaction medium including a therapeutic compound and a linker compound, wherein the therapeutic compound includes at least two substitutable functional groups. In some embodiments, the at least two substitutable functional groups includes one or more hydroxyl groups, phenoxyl groups, amine groups, carboxyl groups, thiol groups, or combinations thereof. In some embodiments, the method includes functionalizing the at least two substitutable functional groups with the linker compound to form a pro-drug. In some embodiments, the linker compound includes allyl chloroformate, toluenediisocyanate, or combinations thereof. In some embodiments, the linker compound includes an ester group, a urethane group, a carbonate group, or combinations thereof for binding to the therapeutic compound. In some embodiments, the method includes copolymerizing the pro-drug with one or more hydrocarbyl groups, the hydrocarbyl groups including hydrocarbyl monomers, hydrocarbyl oligomers, hydrocarbyl polymers, or combinations thereof.

Some embodiments of the present disclosure are directed to a method of providing local therapeutic effects. In some embodiments, the method includes providing a solution including a poly(pro-drug) of the following Formula I. In some embodiments, the method includes casting the solution as a polymeric layer. In some embodiments, casting the pro-drug solution as a polymeric layer includes electrospinning the pro-drug solution on a substrate. In some embodiments, the method includes implanting the polymeric layer in a patient at a location in need of a desired effect of the therapeutic compound. In some embodiments, the method includes degrading the poly(pro-drug) at physiological temperature and pH to release the one or more therapeutic compounds at a rate of about 0.01% and about 0.25% per day.

DETAILED DESCRIPTION

Figure 1A:
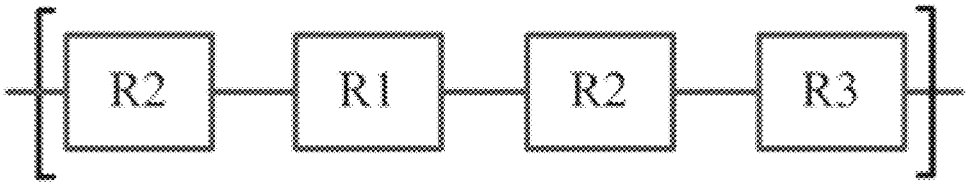
FIGS. 1A-1B are a schematic representations of chemical structures of poly(pro-drug) materials according to some embodiments of the present disclosure.
Figure 1B:
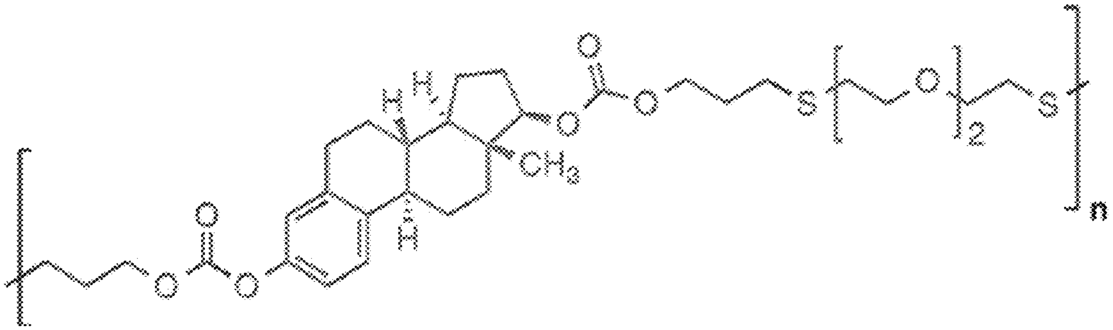

Referring now to FIGS. 1A-1B, aspects of the disclosed subject matter include a poly(pro-drug) material including one or more polymers. In some embodiments, the polymers include a structure according to following formula:

(Formula I)

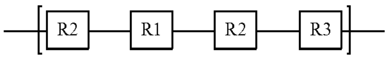

In some embodiments, the polymers have an average molecular weight between about 50 kDa and about 120 kDa. In some embodiments, the polymers have an average molecular weight between about 60 kDa and about 110 kDa. In some embodiments, the polymers have an average molecular weight between about 70 kDa and about 100 kDa. In some embodiments, the polymers have an average molecular weight between about 80 kDa and about 90 kDa.

In some embodiments, R1 of Formula I includes one or more therapeutic compounds. In some embodiments, R1 includes a plurality of therapeutic compounds. In some embodiments, R1 includes two or more different therapeutic compounds. In some embodiments, the therapeutic compound includes an estrogen, curcumin, fingolimod, or combinations thereof. In some embodiments, the polymers include more than about 25 therapeutic compounds, on average. In some embodiments, the polymers include more than about 50 therapeutic compounds, on average. In some embodiments, the polymers include more than about 100 therapeutic compounds, on average. In some embodiments, the polymers include more than about 150 therapeutic compounds, on average.

In some embodiments, R2 of Formula I includes one or more linkers. In some embodiments, the one or more linkers include chemical compounds. In some embodiments, the one or more linkers are cleavable, e.g., via hydrolytic degradation. In some embodiments, the one or more linkers include an ester, a urethane, a carbonate, or combinations thereof bound to the therapeutic compound.

In some embodiments, R3 of Formula I includes one or more hydrocarbyl groups. As used herein, the term "hydrocarbyl" is used to refer to saturated and unsaturated hydrocarbon compounds, including chains, rings, or combinations thereof, and can also include amounts of oxygen, sulfur, nitrogen, etc. In some embodiments, the hydrocarbyl group includes at least 2, 4, 6, 8, 10, 12, 14, 16, or 18 carbons. In some embodiments, the hydrocarbyl group includes more than 18 carbons. In some embodiments, the hydrocarbyl group includes poly(ethylene glycol), poly(ethylene glycol) dithiol, or combinations thereof. In some embodiments, the one or more hydrocarbyl groups is biodegradable.

Figure 2:
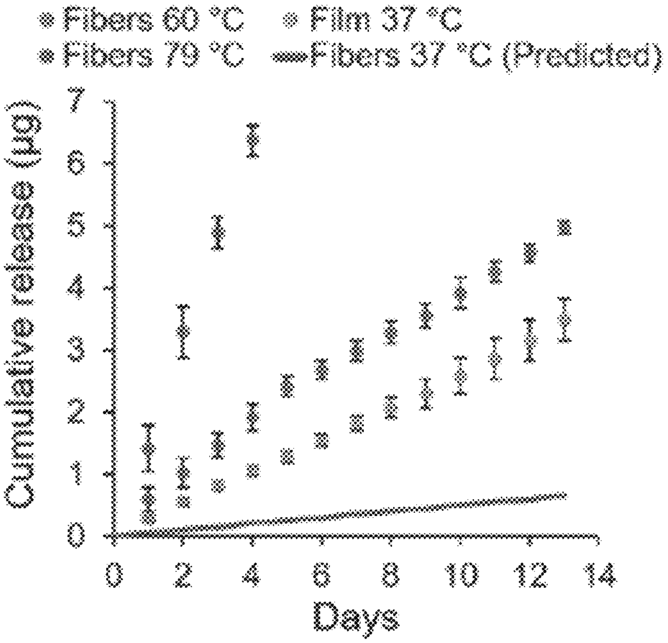
FIG. 2 is a graph portraying a release profile of therapeutic compounds from poly(pro-drug) materials according to some embodiments of the present disclosure.

In some embodiments, the polymers include a structure according to the following formula:

In some embodiments, the therapeutic compound is released from the poly(pro-drug) material by degrading the linkers, the hydrocarbyl groups, bonds between the therapeutic compounds and the linkers, the bonds between the linkers and the hydrocarbyl groups, or combinations thereof. In some embodiments, the poly(pro-drug) material is degraded by aqueous media. In some embodiments, the degradation includes hydrolysis of the linkers, the hydrocarbyl groups, the bonds between the therapeutic compound and the linkers, the bonds between the linker and the hydrocarbyl groups, or combinations thereof. Referring now to FIG. 2, some embodiments of the poly(pro-drug) material of the present disclosure advantageously degrade over time scales significantly longer than those previously disclosed in the art. This slow degradation enables the poly(pro-drug) material to degrade in vivo over the course of several months to several years. The slow degradation of the polymeric network thus prolongs release of the therapeutic compound into the surrounding environment because the therapeutic compound is incorporated into the degrading polymeric network itself. As shown in FIG. 2, the release profile of therapeutic compounds from the poly(pro-drug) materials according to some embodiments of the present disclosure are generally linear. In some embodiments, the poly(pro- (Formula II)

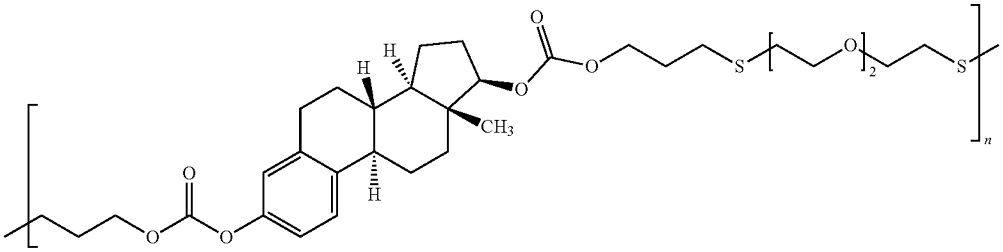

In some embodiments, n is greater than about 25. In some embodiments, n is greater than about 50. In some embodiments, n is greater than about 100. In some embodiments, n is greater than about 150.

In some embodiments, the poly(pro-drug) material includes a plurality of polymers according to Formulas I and/or II to form a polymer network. In some embodiments, at least some of the polymers in the polymer network are crosslinked. In some embodiments, the polymers of the polymer network are generally aligned. In some embodiments, the therapeutic compound has generally uniform distribution across the polymer network. In some embodiments, the therapeutic compound has a nonuniform distribution across the polymer network. In some embodiments, all therapeutic compounds in the polymer network have the same intended therapeutic effect. In some embodiments, the polymer network includes a first therapeutic compound and a second therapeutic compound, the first therapeutic compound having a different therapeutic effect than the second therapeutic compound. In some embodiments, these effects are provided locally, systemically, or combinations thereof. In some embodiments, the therapeutic effect is anti-inflammatory, cell reactivity, antioxidative, cytotoxic, anticytotoxic, etc., or combinations thereof. In some embodiments, the polymers include one or more side chains. In some embodiments, the one or more side chains include hydrocarbyl groups, ionic groups, or combinations thereof.

drug) material has a therapeutic compound release rate of about 0.01% and about 0.25% per day at physiological temperature and pH.

Figure 3:
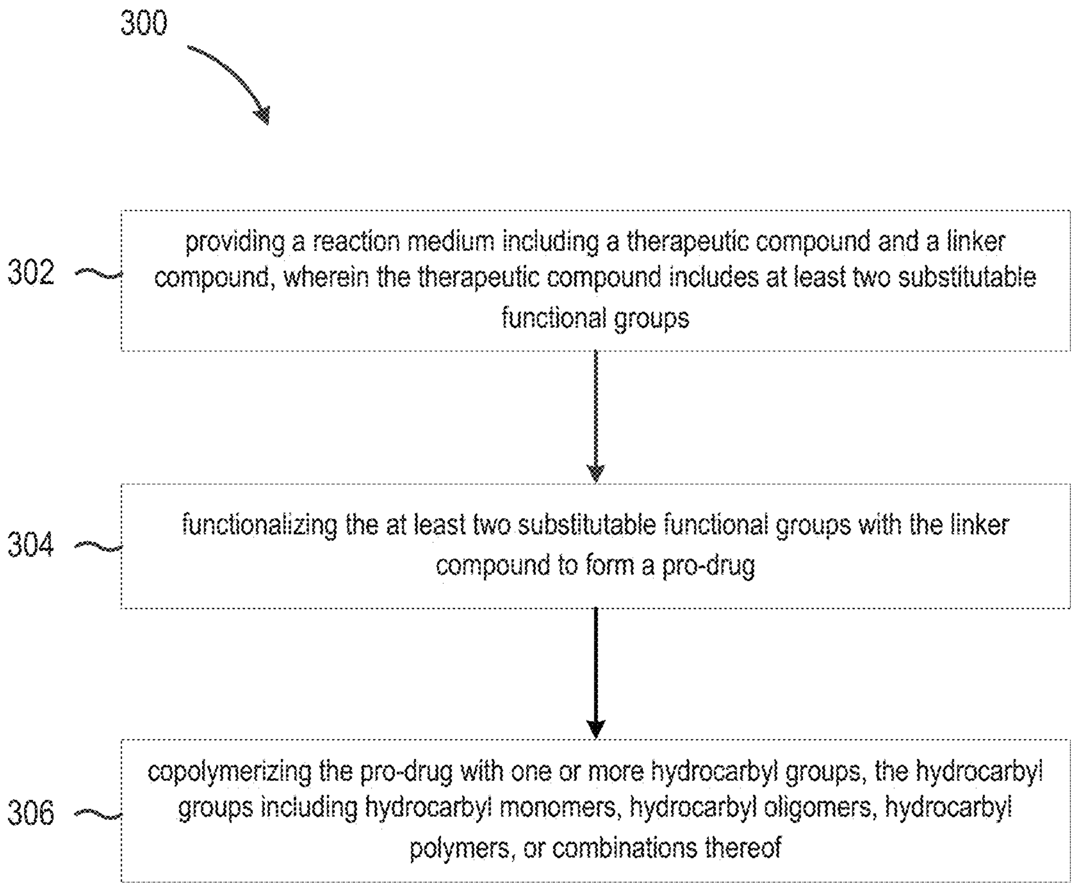
FIG. 3 is a chart of a method of making poly(pro-drug) materials according to some embodiments of the present disclosure.

Referring now to FIG. 3, some embodiments of the present disclosure are directed to a method 300 of making a poly(pro-drug) material such as that described above. At 302, a reaction medium is provided. In some embodiments, the reaction medium includes a therapeutic compound and a linker compound. In some embodiments, the reaction medium includes two or more different therapeutic compounds. In some embodiments, the therapeutic compound includes at least two substitutable functional groups. In some embodiments, the at least two substitutable functional groups include one or more hydroxyl groups, phenoxyl groups, amine groups, carboxyl groups, thiol groups, or combinations thereof. In some embodiments, the therapeutic compound includes an estrogen, curcumin, fingolimod, or combinations thereof. In some embodiments, the linker compound includes one or more ester groups, urethane groups, carbonate groups, or combinations thereof for binding to the therapeutic compound. In some embodiments, the linker compound includes allyl chloroformate, toluenediisocyanate, or combinations thereof.

At 304, the at least two substitutable functional groups are functionalized with the linker to form a pro-drug. At 306, the pro-drug is copolymerized with one or more hydrocarbyl groups. In some embodiments, the hydrocarbyl groups include hydrocarbyl monomers, hydrocarbyl oligomers, hydrocarbyl polymers, or combinations thereof. In some embodiments, the hydrocarbyl group includes polyethylene glycol), polyethylene glycol) dithiol, or combinations thereof. The relatively simple reaction pathways can be used to tune both the stiffness of the poly(pro-drug) material and release of therapeutic compounds from that material. In some embodiments, the stiffness of the poly(pro-drug) material is reduced by use of longer hydrocarbyl groups between the therapeutic compounds.

Figure 4A:
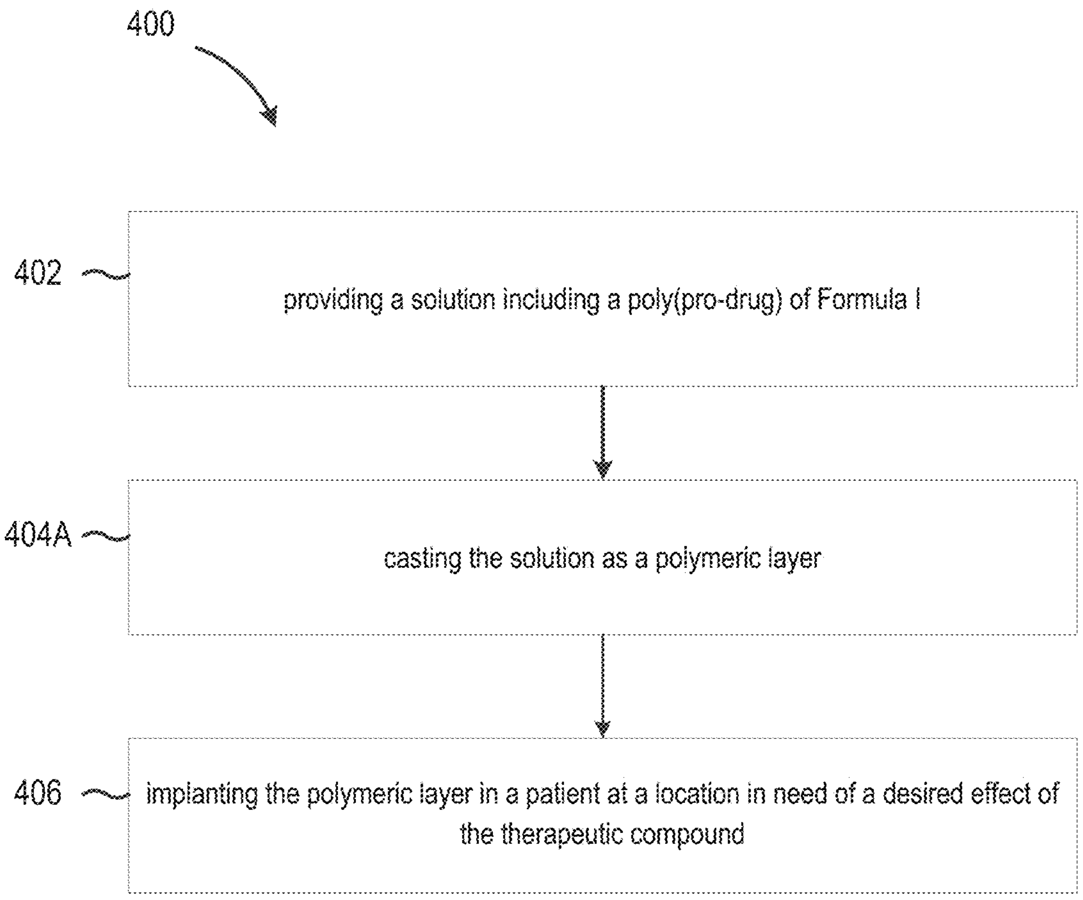
FIGS. 4A-4B are charts of methods of providing therapeutic effects from poly(pro-drug) materials according to some embodiments of the present disclosure.
Figure 4B:
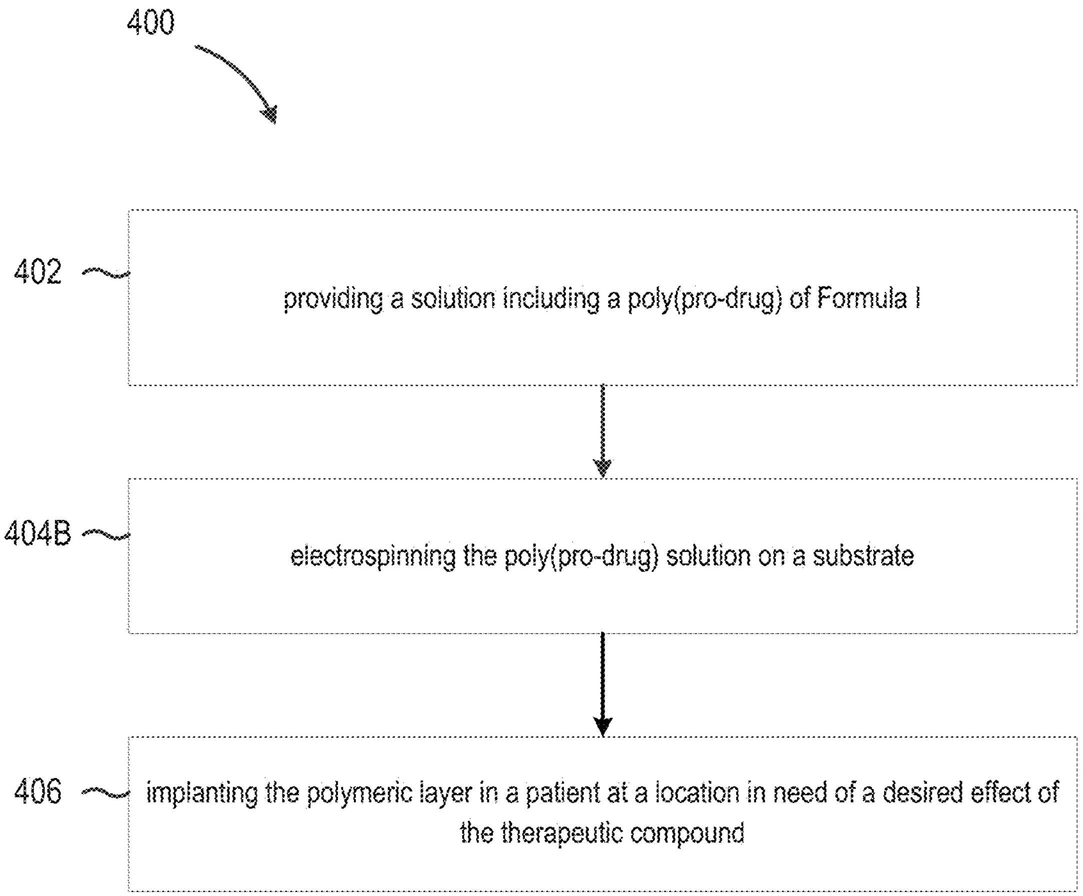

Referring now to FIGS. 4A-4B, some embodiments of the present disclosure are directed to a method 400 of providing therapeutic effects. In some embodiments, these effects are provided locally, systemically, or combinations thereof. As discussed above, in some embodiments, the therapeutic effect is anti-inflammatory, cell reactivity, antioxidative, cytotoxic, anticytotoxic, etc., or combinations thereof. At 402, a solution is provided that includes a poly(pro-drug) of the following Formula I:

(Formula I)

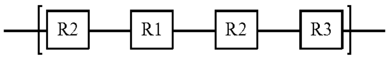

As discussed above, in some embodiments, R1 includes one or more therapeutic compounds, R2 includes one or more cleavable linker compounds, and R3 includes one or more biodegradable hydrocarbyl groups. At 404A, the solution is cast as a polymeric layer. In some embodiments, the polymeric layer is shaped into a film, a tube, a stent, a fiber, other structure, etc., or combinations thereof. Referring now specifically to FIG. 4B, in some embodiments, casting the pro-drug solution as a polymeric layer includes depositing 404B the pro-drug solution on a substrate. In some embodiments, the polymeric layer is dip coated, electrospun, or combinations thereof. In some embodiments, the substrate is implantable, e.g., is sized, shaped, and composed for implantation in a human, animal, etc. In some embodiments, the substrate includes an electrode, a tube, a stent, a fiber, structure composed of plastic, metallic, or natural materials, etc.

Referring again to both FIGS. 4A-4B, at 406, the polymeric layer is implanted in a patient at a location in need of a desired therapeutic effect of the therapeutic compound. As discussed above, in some embodiments, the therapeutic compound includes an estrogen, curcumin, fingolimod, or combinations thereof.

In some embodiments, the poly(pro-drug) degrades after implanting in the patient, releasing the therapeutic compound into the surrounding tissue. As discussed above, in some embodiments, the poly(pro-drug) releases the one or more therapeutic compounds at a rate of about 0.01% and about 0.25% per day at physiological temperature and pH. Because the implanted poly(pro-drug) is, in part, composed of the therapeutic compound, traditional elements such as carrier polymers or compound loading procedures are no longer needed. The longer release time prolongs the duration of the therapeutic effect, which reduces the frequency of which an implanted structure would need to be replaced and further improves the biocompatibility of the structure.

EXAMPLE

Figure 5A:
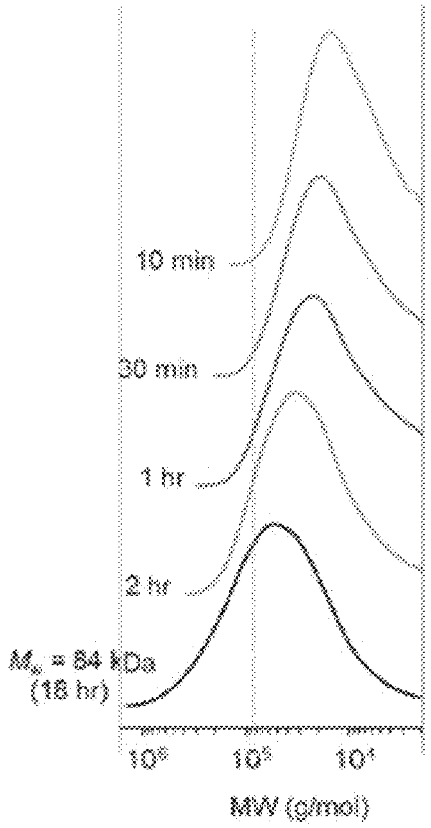
FIG. 5A is a gel permeation chromatography graph confirming formation of poly(pro-drug) materials according to some embodiments of the present disclosure.
Figure 5B:
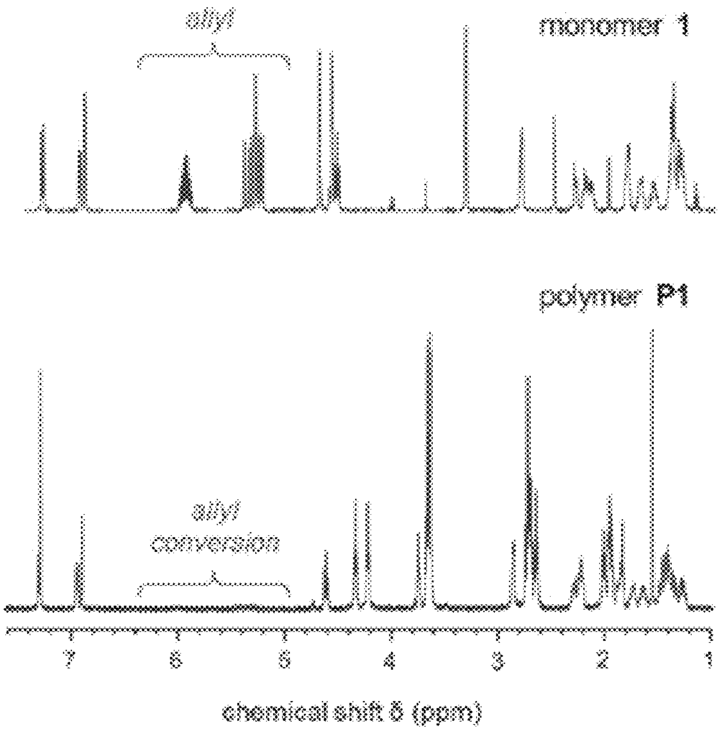
FIG. 5B is a nuclear magnetic resonance graph confirming formation of poly(pro-drug) materials according to some embodiments of the present disclosure.

Samples of a poly(pro-drug) material (P1) consistent with the embodiments described above were prepared. Characterization by gel permeation chromatography (GPC, FIG. 5A) confirmed the formation of high MW polymer (Mw=84 kDa, D=3.73) and the 1H and 13C NMR. (FIG. 5B) were fully consistent with the proposed chemical structure of the polymer.

Figure 6A:
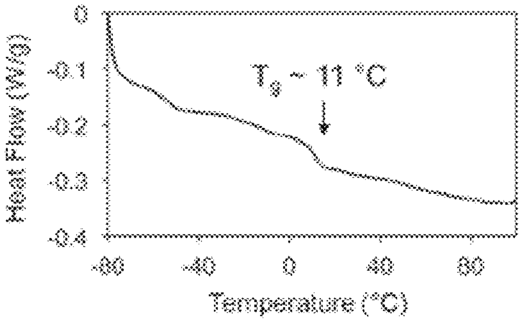
FIG. 6A is a differential scanning calorimetry graph identifying the glass transition temperature of poly(pro-drug) materials according to some embodiments of the present disclosure.
Figure 6B:
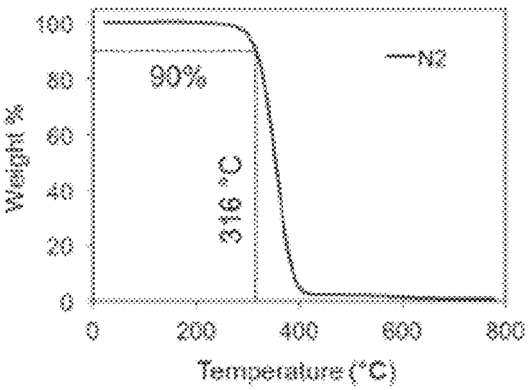
FIG. 6B is a graph showing thermogravimetric analysis of poly(pro-drug) materials according to some embodiments of the present disclosure.

Thermal characterization of the poly(pro-drug) material by DSC revealed a low glass transition temperature ($T_g$~11° C., FIG. 6A), which is consistent with the soft, rubbery properties of this material at room temperature mainly due to the presence of the flexible oligo(ethylene glycol) linker units in the backbone. This property is atypical of polycarbonates, which are more commonly polymers of stiff/rigid units giving rise to a brittle, glassy solid at room temperature. Thermogravimetric Analysis (TGA) showed decomposition beginning at 270° C. (FIG. 6B), which is typical of a synthetic polycarbonate.

Figure 6C:
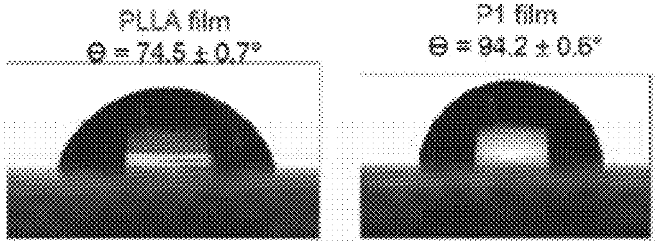
FIG. 6C includes static water contact angle goniometry images for poly(L-lactic acid) films and films according to some embodiments of the present disclosure.
Figure 6D:
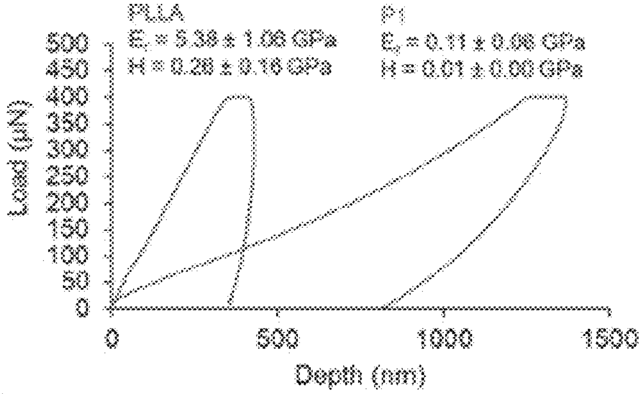
FIG. 6D is a graph of mechanical property characterization via nanoindentation for poly(L-lactic acid) films and films according to some embodiments of the present disclosure.

The hydrophobicity and mechanical properties of the poly(pro-drug) material were compared to poly(L-lactic acid) (PLLA), a polyester commonly used in biomaterials. The poly(pro-drug) material films are modestly hydrophobic (94.2±0.6°) compared to PLLA films (74.5±0.7°), according to static water contact angle goniometry images (FIG. 6C). The observed hydrophobicity of the poly(pro-drug) material films is thus comparable to many common polymeric biomaterials. Nanoindentation (FIG. 6D) demonstrates that the Young's modulus (Er) of the poly(pro-drug) material films (0.11±0.06 GPa) is approximately 49-fold lower than that of PLLA films (5.38±1.06 GPa), and the hardness (H) of P1 (7±3 MPa) is approximately 37-fold lower than that of PLLA (257±158 MPa).

Poly(pro-drug) material fiber degradation was studied under accelerated degradation conditions at 60 and 79° C. (see again FIG. 3), because the very slow hydrolysis rates at 37° C. rendered the detection of full release impractical on the laboratory time scale. As discussed above, at all temperatures studied, a zero-order release profile was observed. By estimating the activation energy from accelerated degradation experiments, the release at 37° C. from micron-scale electrospun fibers was predicted assuming Arrhenius behavior. The poly(pro-drug) material electrospun fibers release 0.21% of the incorporated E2 in a scaffold per day. This predicted release rate translates to poly(pro-drug) material fibers that deliver ~50 ng of E2 daily, corresponding to a ~180 nM concentration in 1 mL of release buffer.

In contrast, thick films of the poly(pro-drug) material release E2 even more slowly in terms of percentages, at a rate of 0.016% of the incorporated E2 mass in the scaffold per day (equivalent to 266±19 ng/day in terms of mass) at 37° C. It would thus require as long as 17 years to fully degrade the entire thin film at physiological temperature and pH. Because the thick films include a much larger absolute quantity of E2 relative to the micron-scale fibers, release of E2 from the films was directly observed.

To examine the bioactivity of E2 released during poly (pro-drug) material degradation and the effects of sustained E2 release on neurons, whole dorsal root ganglion (DRG) were cultured on poly(pro-drug) material films to examine the ability of the poly(pro-drug) material to promote neurite extension. To analyze material-derived neurite extension, DRG were cultured onto three types of scaffolds: 1) PLLA fibers electrospun onto a PLLA film (PLLA/PLLA), 2) PLLA fibers electrospun on to a PLLA film with a 100 nM bolus of exogenous E2 at the beginning of culture (PLLA/PLLA+Exo E2), and 3) PLLA fibers electrospun onto a poly(pro-drug) material film (PLLA/P1). A bolus of E2 was used as a comparison to demonstrate the benefit of sustained E2 release relative to a one-time injection. PLEA fibers were used in this experiment to isolate the effects of E2 released the poly(pro-drug) material as the only factor influencing DRG neurite extension.

Figure 7:
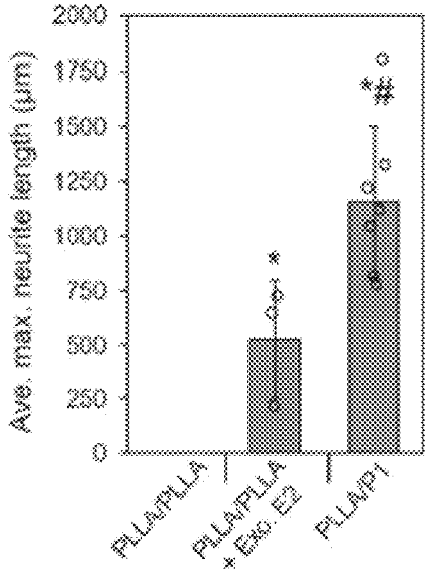
FIG. 7 is a graph portraying induction of neurite growth according to some embodiments of the present disclosure.

The average neurite outgrowth from DRG cultured onto PLEA/P1 scaffolds (1153±347.0 μm) was significantly greater than neurite outgrowth from DRG cultured onto PLLA/PLLA scaffolds (0±0 μm, $p<0.001$, one-way ANOVA) or DRG cultured onto PLLA/PLLA scaffolds with bolus E2 (526.7±273.4 μm, $p=0.028$, one-way ANOVA). These results show that the poly(pro-drug) material induces DRG neurite outgrowth that was significantly greater than the neurite outgrowth observed when a one-time bolus of E2 was administered (FIG. 7).

Methods and systems of the present disclosure are advantageous in that they provide safe, longer-term therapeutic compound release for a variety of applications. Incorporating prolonged-release therapeutic compounds into coatings for implantable structures, or into implantable structures themselves, provides an added therapeutic benefit to these structures. In the case of estrogen as described here, otherwise inert structures can be endowed with neuroprotective and tissue regenerative properties, e.g., at locations having suffered a nerve injury.

In comparison to Estradurin®, the poly(pro-drug) materials of the present disclosure is a substantially longer polymer where the drug is presented as a component of the material itself. The material is also able to cast as a coating on a substrate via multiple processes, such as dip coating or electrospinning. Additionally, the overall reaction scheme allows incorporation of the therapeutic compounds into polycarbonate networks for more sustained release relative to PE, PAE, and PEP.

The longest term estrogen releasing products on the market include Estradurin®, which provides estrogen delivery for approximately one month, and Estring®, which releases estrogen via diffusion for up to 90 days. The control of drug release over years-long time scales is unprecedented in the field, and all components released from the material are generally recognized as safe. The poly(pro-drug) materials also exhibit advantageously reduced stiffness relative to previous materials, increasing their viability as candidates for long-term implantation. Thus, the present disclosure improves upon similar products because the estrogen-release duration is significantly increased, and the material will not need to be removed from a patient since the implantable device will fully degrade over time without any toxic byproducts. In view of the above, the methods and systems of the presents disclosure are enticing for a myriad of biomedical applications, including veterinary medicine, cancer treatments, birth control, and hormone replacement therapy.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A method of making a poly(pro-drug) material, comprising:

copolymerizing a therapeutic compound selected from the group consisting of 17β-estradiol, curcumin and fingolimod with 1) a linker compound selected from the group consisting of allyl chloroformate, toluenediisocyanate, and combinations thereof, and with 2) a polymer selected from the group consisting of poly(ethylene glycol), poly(ethylene glycol) dithiol, and combinations thereof, thereby forming the poly(pro-drug) material.

2. The method according to claim 1, wherein polymers in the poly(pro-drug) material have a molecular weight between about 80 kDa and about 90 kDa.

* * * * *